(12) United States Patent
Spellberg et al.

(10) Patent No.: US 9,169,477 B2
(45) Date of Patent: Oct. 27, 2015

(54) COMPOSITIONS AND METHODS FOR IMMUNIZATION AGAINST BACTERIA EXPRESSING A CARBAPENEMASE

(71) Applicant: Los Angeles Biomedical Research Institute at Harbor-UCLA Medical Center, Torrance, CA (US)

(72) Inventors: Brad J. Spellberg, Rancho Palos Verdes, CA (US); Lin Lin, Rancho Palos Verdes, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 0 days.

(21) Appl. No.: 13/749,499

(22) Filed: Jan. 24, 2013

(65) Prior Publication Data
US 2013/0202616 A1     Aug. 8, 2013

Related U.S. Application Data

(60) Provisional application No. 61/591,793, filed on Jan. 27, 2012.

(51) Int. Cl.
*A61K 39/40* (2006.01)
*C07K 16/12* (2006.01)
*C07K 16/40* (2006.01)
*C12N 9/86* (2006.01)
*A61K 39/00* (2006.01)

(52) U.S. Cl.
CPC .............. *C12N 9/86* (2013.01); *C07K 16/1203* (2013.01); *C07K 16/40* (2013.01); *C12Y 305/02006* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 6,531,508 B1 | 3/2003 | Normura et al. | |
| 2002/0015697 A1 | 2/2002 | Beckman et al. | |
| 2005/0042664 A1* | 2/2005 | Wu et al. | 435/6 |
| 2006/0019279 A1* | 1/2006 | Bosse et al. | 435/6 |
| 2008/0152641 A1* | 6/2008 | Haas et al. | 424/130.1 |
| 2010/0221253 A1 | 9/2010 | Emery et al. | |
| 2011/0189217 A1 | 8/2011 | Barry | |
| 2011/0190138 A1 | 8/2011 | Skubatch | |
| 2011/0236410 A1 | 9/2011 | Bakshi et al. | |
| 2011/0245094 A1 | 10/2011 | Washburn et al. | |

FOREIGN PATENT DOCUMENTS

| | | |
|---|---|---|
| WO | 2011042454 | 4/2011 |
| WO | 2011138402 | 11/2011 |
| WO | 2011160020 | 12/2011 |
| WO | WO 2011/160119 A2 * | 12/2011 |

OTHER PUBLICATIONS

Dumoulin et al. Protein Science. 2002, 11:500-515.*
Sesay, Muctarr Ayoub. 2003. Biopharm International 16(12) (Dec. 2003): 32. Retrieved from http://search.proquest.com/professional/docview/668243181?acccountid=152655.*
Endimiani et al. Journal of Antimicrobial Chemotherapy (2009) 64, 1102-1110.*
Schwarz et al. Methods in Molecular Biology 147:49-56, 2000.*
Hujer et al. Antimicro. Agents Chemother 48:3980-3988, 2004.*
Ake et al., "Gram-Negative Multidrug-Resistant Organism Colonization in a US Military Healthcare Facility in Iraq," Infect. Control Hosp. Epidemiol. 32:545-552 (2011).
Anderson et al., "Evaluation of Methods to Identify the Klebsiella pneumonia Carbapenemase in Enterobacteriaceae," J. Clin. Microbiol. 45:2723-2725 (2007).
Bonomo, "New Delhi Metallo-β-Lactamase and Multidrug Resistance: A Global SOS?" Clin. Infect. Dis. 52:485-487 (2011).
Bradford et al.,"Emergence of Carbapenem-Resistant Klebsiella Species Possessing the Class A Carbapenem-Hydrolyzing KPC-2 and Inhibitor Resistant TEM-30 b-Lactamases in New York City," Clin. Infect. Dis. 39:55-60 (2004).
Bratu et al., "Emergence of KPC-Possessing Klebsiella pneumoniae in Brooklyn, New York: Epidemiology and Recommendations for Detection," Antimicrob Agents Chemother 49:3018-3020 (2005).
Budzikiewcz, "Siderophore-Antibiotic Conjugates Used as Trojan Horses Against Pseudomonas aeruginosa," Curr. Top. Med. Chem. 1(1):73-82 (2001).
Castanheira et al., "Early Dissemination of NDM-1- and OXA-181- Producing Enterobacteriaceae in Indian Hospitals: Report from the SENTRY Antimicrobial Surveillance Program, 2006-2007," Antimicrob. Agents Chemother. 55:1274-8 (2011).
Chen et al., "Emergence of NDM-1-producing Acinetobacter baumannii in China," J. Antimicrob. Chemother. 66:1255-1259 (2011).

(Continued)

*Primary Examiner* — Oluwatosin Ogunbiyi
(74) *Attorney, Agent, or Firm* — Pillsbury Winthrop Shaw Pittman LLP

(57) ABSTRACT

The present invention provides vaccine and pharmaceutical compositions for treating or preventing bacterial inventions. The vaccine compositions of the invention include a carbapenemase such as a serine carbapenemase, a metallo-β-lactamase or an immunogenic fragment thereof. The pharmaceutical compositions include an anti-carbapenemase antibody or fragment thereof. Also provided are methods for treating and preventing a bacterial infection using the vaccine and pharmaceutical compositions of the invention. The invention further provides antibody conjugates that include an antibody or fragment thereof conjugated to a siderophore or an analog thereof.

29 Claims, 5 Drawing Sheets

(56) References Cited

OTHER PUBLICATIONS

Chen et al., "Multiplex Real-Time PCR Assay for Detection and Classification of Klebsiella pneumoniae Carbapenemase Gene (blaKPC) Variants," J. Clin. Microbiol. 49(2):579-585 (2011).
Cuzon et al., "Plasmid-Mediated Carbapenem-Hydrolyzing-Lactamase KPC-2 in Klebsiella pneumoniae Isolate from Greece," Antimicrob. Agents Chemother. 52:796-797 (2008).
Deshpande et al., "Emergence of serine carbapenemases (KPC and SME) among clinical strains of Enterobacteriaceae isolated in the United States Medical Centers:Report from the MYSTIC Program (1999-2005)," Diagn. Microbiol. Infect. Dis. 56:367-372 (2006).
Franklin et al., "Phenotypic Detection of Carbapenem-Susceptible Metallo-Lactamase-Producing Gram-Negative Bacilli in the Clinical Laboratory," J. Clin. Microbiol. 44:3139-3144 (2006).
Gasink et al., "Risk Factors and Clinical Impact of Klebsiella pneumoniae Carbapenemase-Producing K. pneumonia," Infect. Control Hosp. Epidemiol. 30:1180-1185 (2009).
Gootz et al. "Genetic Organization of Transposase Regions Surrounding blaKPC Carbapenemase Genes on Plasmids from Klebsiella Strains Isolated in a New York City Hospital," Antimicrob. Agents Chemother. 53:1998-2004 (2009).
Kitchel et al., "Molecular Epidemiology of KPC-Producing Klebsiella pneumonia Isolates in the United States: Clonal Expansion of Multilocus Sequence Type," Antimicrob. Agents Chemother. 53:3365-3370 (2009).
Kitchel et al., "Regioual Dissemination of KPC-Producing Klebsiella pneumonia," Antimicrob. Agents Chemother. 53:4511-4513 (2009).
Kumarasamy et al., "Emergence of a new antibiotic resistance mechanism in India, Pakistan, and the UK: a molecular, biological, and epidemiological study," Lancet Infect. Dis. 10:597-602 (2010).
Moellering et al., "NDM-1—A Cause for Worldwide Concern," N. Engl. J. Med. 363:2377-2379 (2010).
Mushtaq et al., "Phylogenetic diversity of Escherichia coli strains producing NDM-type carbapenemases," J. Antimicrob. Chemother. 66:2002-2005 (2011).
Navon-Venezia et al., "First Report on a Hyperepidemic Clone of KPC-3-Producing Klebsiella pneumonia in Israel Genetically Related to a Strain Causing Outbreaks in the United States," Antimicrob. Agents Chemother. 53:818-820 (2009).
Patel et al., "Outcomes of Carbapenem-Resistant Klebsiella pneumoniae Infection and the Impact of Antimicrobial and Adjunctive Therapies," Infect. Control Hosp. Epidemiol. 29:1099-1106 (2008).
Peirano et al., "New Delhi Metallo-β-Lactamase from Traveler Returning to Canada1," Emerg. Infect. Dis. 17:242-244 (2011).
Poirel et al., "Emergence of Metallo-Lactamase NDM-1-Producing Multidrug-Resistant Escherichia coli in Australia," Antimicrob. Agents Chemother. 54:4914-4916 (2010).
Poirel et al., "Detection of NDM-1-Producing Klebsiella pneumoniae in Kenya," Antimicrob. Agents Chemother. 55:934-936 (2011).
Qi et al., "ST11, the dominant clone of KPC-producing Klebsiella pneumoniae in China," J. Antimicrob. Chemother. 66:307-312 (2011).
Queenam and Bush, "Carbapenemases: the Versatile-Lactamases," Clin. Microbiol. Rev., 20(3): 440-458 (2007).
Schwaber et al. "Predictors of Carbapenem-Resistant Klebsiella pneumoniae Acquisition among Hospitalized Adults and Effect of Acquisition on Mortality," Antimicrob. Agents Chemother. 52:1028-1033 (2008).
Souli et al. "An Outbreak of Infection due to b-Lactamase Klebsiella pneumoniae Carbapenemase 2-Producing K. pneumoniae in a Greek University Hospital: Molecular Characterization, Epidemiology, and Outcomes," Clin. Infect. Dis. 50:364-373 (2010).
Stimmel et al., "Site-specific Conjugation on Serine 3 Cysteine Variant Monoclonal Antibodies," J. Biol. Chem. 275:30445-30450 (2000).
Struelens et al., "New Delhi metallo-beta-lactamase 1-producing Enterobacteriaceae: emergence and response in Europe," Euro. Surveill. 15(46): pii: 19716 (2010).
Sutter et al., "High Incidence of Multidrug-Resistant Gram-Negative Bacteria Recovered from Afghan Patients at a Deployed US Military Hospital," Infect. Control Hosp. Epidemiol. 32:854-860 (2011).
Tato et al., "Complex Clonal and Plasmid Epidemiology in the First Outbreak of Enterobacteriaceae Infection Involving VIM-1 Metallo-b-Lactamase in Spain: Toward Endemicity?," Clin. Infect. Dis. 47:1117-1178 (2007).
Tijet et al., "New Delhi Metallo-β-Lactamase, Ontario, Canada," Emerg. Infect. Dis. 17:306-307 (2011).
Turnidge et al., "Setting and Revising Antibacterial Susceptibility Breakpoints," Clin. Microbiol. Rev. 20:391-408 (2007).
Villegas et al., "First Detection of the Plasmid-Mediated Class A Carbapenemase KPC-2 in Clinical Isolates of Klebsiella pneumoniae from South America," Antimicrob. Agents Chemother. 50:2880-2882 (2006).
Walsh et al., "Dissemination of NDM-1 positive bacteria in the New Delhi environment and its implications for human health: an environmental point prevalence study," Lancet Infect. Dis. 11:355-362 (2011).
Woodford et al., "Outbreak of Klebsiella pneumoniae Producing a New Carbapenem-Hydrolyzing Class A-Lactamase, KPC-3, in a New York Medical Center," Antimicrob. Agents Chemother. 48:4793-4799 (2004).
Yamamoto et al., "Emergence of NDM-1-positive capsulated Escherichia coli with high resistance to serum killing in Japan ," J. Infect. Chemother. 17:435-439 (2011).
Yegit et al., "Novel Carbapenem-Hydrolyzing b-Lactamase, KPC-1, from a Carbapenem-Resistant Strain of Klebsiella pneumonia," Antimicrob. Agents Chemother., 45:1151-1161 (2001).
Yong et al., "Characterization of a New Metallo-Lactamase Gene, blaNDM-1, and a Novel Erythromycin Esterase Gene Carried on a Unique Genetic Structure in Klebsiella pneumoniae Sequence Type 14 from India," Antimicrob. Agents Chemother. 53:5046-5054 (2009).
Zarkotou et al., "Predictors of mortality in patients with bloodstream infections caused by KPC-producing Klebsiella pneumoniae and impact of appropriate antimicrobial treatment," Clin. Microbiol. Infect. 17(2):1798-1803 (2011).
Molecular Probes, "No better time to react—New reactive dyes and chemicals," Bioprobes, 45:23-27 (2007).

* cited by examiner

COMPOSITIONS AND METHODS FOR IMMUNIZATION AGAINST BACTERIA EXPRESSING A CARBAPENEMASE

This application claims the benefit of priority of U.S. Provisional application Ser. No. 61/591,793, filed Jan. 27, 2012, the entire contents of which is incorporated herein by reference.

BACKGROUND OF THE INVENTION

The present invention relates generally to compositions and methods for treating or preventing bacterial infections, and more specifically to treating or preventing infections caused by extreme drug resistant bacteria expressing a carbapenemase.

In the last decade, multi-drug resistant organisms have become endemic in healthcare systems throughout the world. Of highest priority for new treatment strategies are infections caused by extreme drug resistant (XDR) gram negative bacilli, which are resistant to carbapenems and all other antibiotics except for colistin or tigecycline. For example, infections caused by XDR *Klebsiella pneumoniae* that express the serine carbapenemase *K. pneumonia* carbapenemase (KPC) have spread across the United States. Moreover, infections caused by these KPC bacteria are associated with an approximate 50% mortality rate. Like KPC, a recently identified metallo-β-lactamase resistance mechanism termed the New Delhi metallo-β-lactamase (NDM-1), which is spread by transmissible plasmids, has been found globally. For example, NDM-1 bacteria have been found in Asia, Western Europe and the United States. The global health concerns regarding these bacteria are even further exacerbated by the dearth of drugs in the commercial pipeline that may have activity against these organisms.

KPC-expressing *K. pneumoniae* are increasingly common and cause substantial morbidity and mortality. The initial outbreak of carbapenem-resistant *K. pneumoniae* expressing the KPC enzyme occurred in North Carolina in 1996. Yigit et al., *Antimicrob. Agents Chemother.* 45:1151-1161 (2001). Shortly thereafter the organism appeared in New York City, where it has since become endemic in hospitals. Bratu et al., *Antimicrob Agents Chemother.* 49:3018-3020 (2005); Gootz et al. *Antimicrob. Agents Chemother.* 53:1998-2004 (2009); Bradford et al., *Clin. Infect. Dis.* 39:55-60 (2004) and Woodford et al., *Antimicrob. Agents Chemother.* 48:4793-4799 (2004). For example, in just two months, four hospitals in Brooklyn, N.Y. cultured more than sixty KPC-expressing isolates of *K. pneumoniae*, which represented a quarter of all the *K. pneumoniae* isolates encountered. Bratu et al., supra. Subsequently KPC-expressing isolates spread to most states in the United States, as well as through Europe, Asia, and Latin America. Kitchel et al., *Antimicrob. Agents Chemother.* 53:3365-3370 (2009); Zarkotou et al., *Clin. Microbiol. Infect.* 17(2):1798-1803 (2011); Cuzon et al., *Antimicrob. Agents Chemother.* 52:796-797 (2008); Navon-Venezia et al., *Antimicrob. Agents Chemother.* 53:818-820 (2009); Kitchel et al., *Antimicrob. Agents Chemother.* 53:4511-4513 (2009); Qi et al., *J. Antimicrob. Chemother.* 66:307-312 (2011); Villegas et al., *Antimicrob. Agents Chemother.* 50:2880-2882 (2006); and Deshpande et al., *Diagn. Microbiol. Infect. Dis.* 56:367-372 (2006). The US Centers for Disease Control reported the molecular typing results of strains they had accumulated from thirty-three US states, as well as Israel and India. Kitchel et al., *Antimicrob. Agents Chemother.* 53:3365-3370 (2009). A single strain type, ST 258, accounted for 70% of these isolates.

The most common sites of infection caused by KPC-expressing bacteria include the lung, the blood, and the abdomen, although other sites may be involved as well (e.g., urine and wounds). Gasink et al., *Infect. Control Hosp. Epidemiol.* 30:1180-1185 (2009). By multivariate analysis, risk factors for acquisition of KPC-expressing *K. pneumoniae*, compared to carbapenem-susceptible bacteria, included severe illness (odds ratio [OR] 4), prior fluoroquinolone use (OR 3), and prior extended-spectrum cephalosporin use (OR 3). Gasink et al., supra; and Schwaber et al. *Antimicrob. Agents Chemother.* 52:1028-1033 (2008). In another study, infection caused by KPC-expressing *K. pneumoniae* was independently associated with receipt of mechanical ventilation, longer length of stay before infection, and exposure to cephalosporins and carbapenems. Patel et al., *Infect. Control Hosp. Epidemiol.* 29:1099-1106 (2008).

In multiple studies, infection caused by KPC-producing *K. pneumoniae* was independently associated with in-hospital mortality. In several case control studies, absolute in hospital mortality rates of patients infected with KPC-expressing *K. pneumoniae* ranged from 32 to 44% versus 9 to 13% mortality rates for infections caused by carbapenem-susceptible *K. pneumoniae*. Gasink et al., supra; Schwaber et al., supra; and Patel et al., supra. In a case series from New York, the in hospital mortality of patients bacteremic with KPC-expressing *K. pneumoniae* was ~50%. Bratu et al., supra; Zarkotou et al., supra; and Patel et al., supra. The mortality was even worse (61%) in patients infected with KPC-expressing *K. pneumoniae* who received initially ineffective therapy. Zarkotou et al., supra. In another case series, the mortality rate of patients infected by KPC-expressing *K. pneumoniae* was 59% among patients in the intensive care unit and 38% among non-ICU patients. Souli et al. *Clin. Infect. Dis.* 50:364-73 (2010).

Even worse outcomes are seen with truly pan-drug resistant strains. For example, in a case control study of patients with colistin susceptible vs. colistin resistant KPC expressing *K. pneumoniae*, the mortality rate of patients with colistin-susceptible strains was 54%. Zarkotou et al., supra. By comparison, the mortality rate of patients with colistin-resistant strains was an alarming 75%. These unacceptably high mortality rates, and the rising incidence of KPC-expressing strains and pan-resistance among those strains, underscore the need for new therapeutic strategies to deal with these infections.

NDM-1-expressing gram negative bacteria are also spreading rapidly and globally. The initial description of NDM-1 occurred in a Swedish patient of Indian descent who acquired a urinary tract infection (UTI) during a trip to New Delhi. Yong et al., *Antimicrob. Agents Chemother.* 53:5046-5054 (2009). The follow up case series described isolates of both *E. coli* and *K. pneumoniae* expressing NDM-1 found throughout India. Kumarasamy et al., *Lancet Infect. Dis.* 10:597-602 (2010). Numerous patients brought their infections back to Europe. The strains were all resistant to all antibiotics except tigecycline and colistin, and up to 10% of the strains were resistant to both of these antibiotics and were pan-drug resistant (PDR) strains. Since then bacteria from numerous other genera, including *Enterobacter, Acinetobacter, Shigella, Vibrio, Aeromonas,* and *Pseudomonas,* have been described to express NDM-1. Moreover, these organisms have been found throughout China, Japan, Europe, Africa, Canada, Australia, and in the United States. Moellering et al., *N. Engl. J. Med.* 363:2377-2379 (2010); Castanheira et al., *Antimicrob. Agents Chemother.* 55:1274-8 (2011); Poirel et al., *Antimicrob. Agents Chemother.* 54:4914-4916 (2010); Poirel et al., *Antimicrob. Agents Chemother.* 55:934-936 (2011); Struelens et al., *Euro. Surveill.* 15(46): pii: 19716 (2010); Bonomo, *Clin. Infect. Dis.* 52:485-487 (2011); Tijet et al., *Emerg. Infect. Dis.* 17:306-307 (2011); Chen et al., *J. Antimicrob. Chemother.* 66:1255-1259 (2011); and Yamamoto et al., *J. Infect. Chemother.* 17:435-439 (2011). NDM-1-expressing gram negative bacilli have also been cultured from foreign nationals cared for in forward deployed military medical units, creating potential for their transfer to US military personnel. Ake et al., *Infect. Control Hosp. Epidemiol.* 32:545-552 (2011); and Sutter et al., *Infect. Control Hosp. Epidemiol.* 32:854-60 (2011).

In addition to spreading into multiple genera, individual *E. coli* strains expressing NDM-1 have been found to be of multiple strain types, underscoring the ecological diversity of the resistance mechanism. Mushtaq et al., *J. Antimicrob. Chemother.* 66:2002-2005 (2011). Unfortunately, diverse genera expressing NDM-1 have been found widely distributed in environmental sources throughout India, underscoring the ability of the organism to spread in communities outside of a healthcare setting. Walsh et al., *Lancet Infect. Dis.* 11:355-362 (2011); and Peirano et al., *Emerg. Infect. Dis.* 17:242-244 (2011). NDM-1 will likely continue to spread both in communities and in healthcare settings in the United States, and throughout the world.

Thus, new ways to prevent or treat infections caused by XDR gram negative bacilli are needed. This invention satisfies this need and provides related advantages.

SUMMARY OF INVENTION

In accordance with the present invention, herein provided are vaccine compositions for treating or preventing bacterial inventions. The vaccine compositions of the invention include a carbapenemase such as a serine carbapenemase, a metallo-β-lactamase or an immunogenic fragment thereof.

The invention also provides methods for treating and preventing a bacterial infection in a subject by administering a vaccine composition of the invention to the subject. The invention methods include treating or preventing bacterial infections caused by gram negative bacilli, in particular extreme drug resistant (XDR) bacilli, that express a serine carbapenemase or a metallo-β-lactamase.

The invention also provides pharmaceutical compositions having an anti-carbapenemase antibody, such as an anti-serine carbapenemase or an anti-metallo-β-lactamase antibody, or a fragment thereof. In particular, the invention provides anti-serine carbapenemase antibodies having anti-KPC activity and anti-metallo-β-lactamase antibodies having anti-NDM-1 activity.

Still further, the invention provides methods of treating or preventing a bacterial infection in a subject by administering a therapeutically effective amount of a pharmaceutical composition of the invention. The methods of the invention using such pharmaceutical compositions include treating or preventing bacterial infections caused by gram negative bacilli, in particular extreme drug resistant (XDR) bacilli that express a serine carbapenemase or a metallo-β-lactamase.

The invention also provides methods for increasing or restoring the efficacy of an antibiotic. The methods of the invention can include contacting a bacterial cell with an effective amount of an anti-carbapenemase antibody of the invention, such as an anti-serine carbapenemase antibody or an anti-metallo-β-lactamase antibody, or a fragment thereof. These methods are particularly effective in increasing or restoring the efficacy of β-lactam antibiotics, such as antibiotics of the carbapenem and penem class.

The invention still further provides antibody conjugates that include an antibody or fragment thereof conjugated to a siderophore or an analog thereof. The antibody conjugates of the invention can be conjugated with a siderophore, such as enterobactin, which can increase bacterial uptake of the antibody or fragment thereof. The antibody conjugates of the invention can also include antibody fragments conjugated with a siderophore. Particularly effective antibody fragment conjugates of the invention include Fabc fragments conjugated with enterobactin.

DETAILED DESCRIPTION OF THE INVENTION

Figure 1:
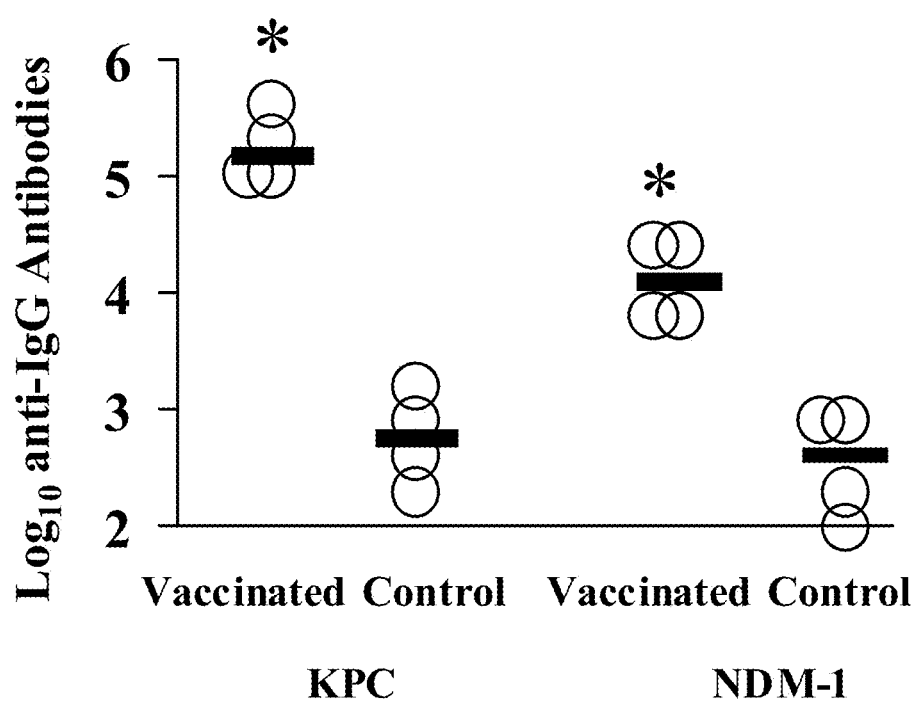
FIG. 1 shows that mice vaccinated with rKPC or rNDM1 generated high titers of IgG. IgG antibody titers in serum from vaccinated or control mice were measured. *$p<0.05$.

The compositions and methods disclosed herein are based, at least in part, on the discovery that pathogenic XDR bacilli expressing *K. pneumonia* carbapenemase (KPC) or New Delhi metallo-β-lactamase (NDM-1) can be killed using anti-KPC or anti-NDM-1 antibodies. The antibacterial activity of the antibodies was particularly effective when bacterial uptake of the purified IgG was enhanced by conjugating IgG to an iron siderophore. The complexed immune IgG-siderophore, but not control IgG, killed NDM-1-expressing *K. pneumoniae*. In addition, siderophore conjugation to immune IgG Fabc fragments, formed by reducing the disulfide bonds at the IgG heavy chain hinge region, killed both NDM-1- and KPC-expressing strains. Thus, anti-carbapenemase antibodies can kill these bacteria.

The mechanism by which anti-NDM-1 IgG kills the bacteria in vitro is unclear. However, without being bound by theory, it is contemplated that conjugation to the siderophore increases cidal activity either by increasing uptake of the antibody into the periplasmic space wherein the target carbepenemase is located, or by physically plugging the siderophore uptake channel, thereby blocking iron uptake. Accordingly, the invention also provides that the anti-carbepenemase antibodies can synergize with carbapenems by neutralizing carbepenemase activity, thereby restoring susceptibility to the antibiotics.

The enhanced uptake via siderophores is particularly effective for targeting antibiotic resistance because many antibiotic resistance targets exist in the periplasmic space, which is also the immediate location siderophores are deposited. Thus, targeting resistance with anti-carbepenemase antibodies is an entirely new approach to attacking XDR pathogens.

Accordingly, in some embodiments, the invention provides a vaccine composition having a protein of the carbapenemase class or an immunogenic fragment thereof and a pharmaceutically acceptable carrier. The carbapenemase class of enzymes recognize almost all hydrolysable β-lactams, and are usually resilient against inhibition by most commercially viable β-lactamase inhibitors. A carbapenemase is also known in the art as a cabapenem-hydrolyzing enzyme and is understood by one of skill in the art to include enzymes of this class that have the functional activity of hydrolyzing antibiotics such as penicillins, cephalosporins, monobactams, and carbapenems. Carbapenemases are members of the molecular class A, B, C and D β-lactamases. Class A and D enzymes have a serine-based hydrolytic mechanism, while class B enzymes are metallo-β-lactamases that contain zinc in the active site. The class C enzyme is a single plasmid-mediated AmpC beta-lactamase, CMY-10, identified in an *Enterobacter aerogenes* isolate. CMY-10 has been shown to be a cephaslosporinase with some carbapenemase properties and is active on a wide spectrum of substrates. The class D carbapenemases consist of OXA-type β-lactamases frequently detected in *Acinetobacter baumannii*. The class A serine carbapenemase group includes members of the *K. pneumonia* carbapenemase (KPC), *Serratia marcescens* enzyme (SME), imipenem-hydrolyzing β-lactamase (IMI), not metalloenzyme carbapenemase (NMC-A), integron-borne cephalosporinase (IBC) and Guiana extended spectrum (GES) enzyme families. The metallo-β-lactamases belong to the New Delhi metallo-β-lactamase (NDM-1), BCII metallo-β-lactamase, Verona integron-encoded (VIM) metallo-β-lactamase, active on imipenem (IMP) metallo-β-lactamase, German imipenemase (GIM) metallo-β-lactamase and Seoul imipenemase (SIM) metallo-β-lactamase families and have been detected in *Pseudomonas aeruginosa* and Enterobacteriaceae.

Accordingly, the vaccine compositions of the invention can include a carbapenemase of any one of the molecular class A β-lactamases, i.e. a serine carbapenemase. For example, in one embodiment of the invention, the vaccine composition includes a serine carbapenemase or immunogenic fragment thereof and a pharmaceutically acceptable carrier. In one aspect of the invention, the serine carbapenemase included in the vaccine composition can be, for example, a *K. pneumonia* carbapenemase (KPC), a *Serratia marcescens* enzyme (SME), a imipenem-hydrolyzing β-lactamase (IMI), a not metalloenzyme carbapenemase (NMC-A), an integron-borne cephalosporinase (IBC) or a Guiana extended spectrum (GES) enzyme. Specific serine carbapenemases that can be used in the vaccine compositions of the invention include any one of serine carbapenemases that are well known in the art. Several exemplary serine carbapenemases and their corresponding encoding nucleic acids are discussed in Queenam and Bush, *Clin. Microbiol. Rev.*, 20(3): 440-458 (2007), which is hereby incorporated by reference.

In some aspects of the invention, a vaccine composition can include a specific serine carbapenemase, such as KPC. Multiple KPC variants are known in the art and have been isolated from several species including *Klebsiella pneumoniae, Enterobacter cancerogenus, Pseudomonas aeruginosa, Escherichia coli* and *Acinetobacter baumannii*. Ten KPC gene variants are presently known in the art. Chen et al., J. Clin. Microbiol. 49(2):579-585 (2011), which is herein incorporated by referenced. These variants include KPC-2 (also known as KPC-1, which is a separate clinical isolate that has the identical nucleotide sequence as KPC-2), KPC-3, KPC-4, KPC-5, KPC-6, KPC-7, KPC-8, KPC-9, KPC-10 and KPC-11. Accordingly, in some aspects of the invention, the vaccine composition of the invention can include one or more of the KPC proteins selected from KPC-2, KPC-3, KPC-4, KPC-5, KPC-6, KPC-7, KPC-8, KPC-9, KPC-10 and KPC-11, or an immunogenic fragment thereof.

In some embodiments of the invention, the vaccine composition can include a carbapenemase of any one of the molecular class B β-lactamases, i.e. a metallo-β-lactamase. For example, in one embodiment of the invention, the vaccine composition includes a metallo-β-lactamase or immunogenic fragment thereof and a pharmaceutically acceptable carrier. In one aspect of the invention, the metallo-β-lactamase included in the vaccine composition can be, for example, a New Delhi metallo-β-lactamase (NDM-1), a BCII metallo-β-lactamase, a Verona integron-encoded (VIM) metallo-β-lactamase, an active on imipenem (IMP) metallo-β-lactamase, a German imipenemase (GIM) metallo-β-lactamase or a Seoul imipenemase (SIM) metallo-β-lactamase. Specific metallo-β-lactamase that can be used in the vaccine compositions of the invention include any one of metallo-β-lactamase that are well known in the art. Several exemplary metallo-β-lactamase and their corresponding encoding nucleic acids are reviewed in Queenam and Bush, *Clin. Microbiol. Rev.*, 20(3): 440-458 (2007), which is hereby incorporated by reference.

In some aspects of the invention, a vaccine composition can include a specific metallo-β-lactamase, such as NDM-1. NDM-1 was originally identified in a *Klebsiella pneumoniae* sample contracted in India (Yong et al., *Antimicrob. Agents Chemother.* 53:5046-5054 (2009)), but has spread to China, Japan, Europe, Africa, Canada, Australia, and the United States, as disclosed above. Accordingly, a vaccine composition of the invention can include NDM-1 as originally isolated from *Klebsiella pneumoniae* or a variant thereof. Such NDM-1 variants can include any one of the NDM-1 isolated from *Enterobacter, Acinetobacter, Shigella, Vibrio, Aeromonas,* and *Pseudomonas,* which are well known in the art.

The term "vaccine" refers to a composition that can be administered to an individual to protect the individual against an infectious disease. Vaccines protect against diseases by inducing or increasing an immune response in a subject against the infectious agent that causes the disease. Exemplary infectious diseases amenable to treatment with the vaccines of the invention include severe pneumonia, infections of the urinary tract, infections of the bloodstream and infections of other parts of the body. The vaccine-mediated protection can be humoral and/or cell mediated immunity induced in host when a subject is challenged with, for example, or an immunogenic portion of a protein described herein.

The vaccine of the present invention will contain an immunoprotective quantity of one or more carbapenemase antigens and is prepared by methods well known in the art. The preparation of vaccines is generally described in, for example, M. F. Powell and M. J. Newman, eds., "Vaccine Design (the subunit and adjuvant approach)," Plenum Press (1995); A. Robinson, M. Cranage, and M. Hudson, eds., "Vaccine Protocols (Methods in Molecular Medicine)," Humana Press (2003); and D. Ohagan, ed., "Vaccine Adjuvants: Preparation Methods and Research Protocols (Methods in Molecular Medicine)," Humana Press (2000).

The proteins or immunogenic fragments included in the vaccines of the invention, can include immunogenic epitopes, which can be identified using experimental methods well known in the art. Additionally, computational modeling can also be used to identify immunogenic epitopes. See, for example, Tong et al. (*Brief Bioinform.* 8(2):96-108 (2006)) and Ponomarenko et al. (2008) "B-cell epitope prediction," in *Structural Bioinformatics*, Bourne P E and Gu J (eds) Wiley-Liss; 2 edition, pgs. 849-879. Once an epitope bearing reactivity with an antibody raised against the intact protein is identified, the peptide can be tested for specificity by amino acid substitution at every position and/or extension at both C and/or N terminal ends. Such epitope bearing polypeptides typically contain at least six to fourteen amino acid residues, and can be produced, for example, by polypeptide synthesis using methods well known in the art or by fragmenting an existing protein. With respect to the molecule used as immunogens pursuant to the present invention, those skilled in the art will recognize that the protein can be truncated or fragmented without losing the essential qualities as an immunogenic vaccine. For example, a protein can be truncated to yield an N-terminal fragment by truncation from the C-terminal end with preservation of the functional properties of the molecule as an immunogenic. Similarly, C-terminal fragments can be generated by truncation from the N-terminal end with preservation of the functional properties of the molecule as an immunogenic. Other modifications in accordance with the teachings and guidance provided herein can be made pursuant to this invention to create other polypeptide functional fragments, immunogenic fragments, variants, analogs or derivatives thereof, to achieve the therapeutically useful properties described herein with the native proteins.

Accordingly, the term "immunogenic fragment" as it is used herein refers to a portion of a protein that is recognized by a T-cell and/or B-cell antigen receptor. The immunogenic portion generally includes at least 5 amino acid residues, or alternatively at least 10, or alternatively at least 20, or alternatively at least 30 amino acid residues of a carbapenemase disclosed herein. In some aspects, immunogenic portions can contain a small N- and/or C-terminal fragment (e.g., 5-30 amino acids, preferably 10-25 amino acids).

The vaccine compositions of the invention further contain conventional pharmaceutical carriers. As used herein, the term "pharmaceutically acceptable carrier" encompasses any of the standard pharmaceutical carriers known in the art, such as phosphate buffered saline solution, water and emulsions such as an oil and water emulsion, and various types of wetting agents. These vaccine compositions can be prepared in liquid unit dose forms. Other optional components, e.g., pharmaceutical grade stabilizers, buffers, preservatives, excipients and the like can be readily selected by one of skill in the art. However, the compositions can be lyophilized and reconstituted prior to use. Alternatively, the vaccine compositions can be prepared in any manner appropriate for the chosen mode of administration, e.g., intranasal administration, oral administration, etc. The preparation of a pharmaceutically acceptable vaccine, having due regard to pH, isotonicity, stability and the like, is within the skill of the art.

The immunogenicity of the vaccine compositions of the invention can further be enhanced if the vaccine further comprises an adjuvant substance. Various methods of achieving adjuvant effects for a vaccine are known. General principles and methods are detailed in "Vaccine Design: Innovative Approaches and Novel Strategies", 2011, Rappuoli R. and Bagnoli F. (eds.), Caister Academic Press, and also in "Vaccine Adjuvants and Delivery Systems", 2007, Singh, M. (ed.), John Wiley & Sons, Inc.

The term "adjuvant" is intended to mean a composition with the ability to enhance an immune response to an antigen generally by being delivered with the antigen at or near the site of the antigen. Ability to increase an immune response is manifested by an increase in immune mediated protection. Enhancement of humoral immunity can be determined by, for example, an increase in the titer of antibody raised to the antigen. Enhancement of cellular immunity can be measured by, for example, a positive skin test, cytotoxic T-cell assay, ELISPOT assay for a carbapenemase. Adjuvants are well known in the art. Exemplary adjuvants include, for example, Freud's complete adjuvant, Freud's incomplete adjuvant, aluminum adjuvants, MF59, QS21 an immune modulating adjuvant such as a toxin, a cytokine, and a mycobacterial derivative; an oil formulation, a polymer, a micelle forming adjuvant, a saponin, an immunostimulating complex matrix (ISCOM® matrix), a particle, DDA (dimethyldioctadecylammonium bromide, DNA adjuvants, and an encapsulating adjuvant. Liposome formulations are also known to confer adjuvant effects, and therefore liposome adjuvants are included according to the invention. Adjuvants can facilitate uptake of the vaccine molecules by antigen presenting cells (APCs), such as dendritic cells, and activate these cells.

The carbapenemase proteins or immunogenic fragments thereof used in the vaccine compositions of the invention can be isolated by a variety of methods well-known in the art, for example, recombinant expression systems, precipitation, gel filtration, ion-exchange, reverse-phase and affinity chromatography, and the like. Other well-known methods are described in Deutscher et al., *Guide to Protein Purification: Methods in Enzymology Vol.* 182, (Academic Press, (1990)). Alternatively, the carbapenemase proteins or immunogenic fragments thereof can be obtained using well-known recombinant methods (see, for example, Sambrook et al., "Molecular Cloning: A Laboratory Manual," $3^{rd}$ Edition. Cold Spring Harbor Laboratories, Cold Spring Harbor, N.Y., 2001; and Ausubel et al., "Current Protocols in Molecular Biology," John Wiley and Sons, Baltimore, Md. (1999)). The methods and conditions for biochemical purification of a carbapenemase can be chosen by those skilled in the art, and purification monitored, for example, by an immunological assay or a functional assay.

An example of the means for preparing a carbapenemase is to express nucleic acids encoding a carbapenemase of the invention in a suitable host cell, such as a bacterial cell, a yeast cell, an amphibian cell such as an oocyte, or a mammalian cell, using methods well known in the art, and recovering the expressed protein, again using well-known purification methods. A carbapenemase can also be isolated directly from cells that have been transformed with expression vectors. Alternatively, the carbapenemase can be produced by chemical synthesis. Methods for chemically synthesizing polypeptides are well known in the art and are commercially available.

Recombinantly expressed carbapenemase of the invention can also be expressed as fusion proteins with appropriate fusion partners. An appropriate fusion partner can be an amino acid sequence that is not normally connected to the amino acid sequence such as an heterologous sequence, which serves a particular function or provides additional characteristic to the carbapenemase. Non-limiting examples of suitable heterologous sequences include a detectable marker, a stabilizing domain, a carrier protein for the generation of antibodies, a linker sequence and a sequence that aids in the purification of the protein. Sequences that can aid in the purification of the invention proteins include affinity tags, such as glutathione S transferase (GST) or poly His.

In some embodiments, the invention provides a method for treating or preventing a bacterial infection in a subject in need thereof. The methods of the invention include administering a therapeutically effective amount of a vaccine composition as disclosed here. For example, the vaccine composition can include a protein of the carbapenemase class or an immunogenic fragment thereof. Accordingly, in some aspects, the invention provides a method for treating or preventing a bacterial infection in a subject in need thereof by administering a therapeutically effective amount of a vaccine composition having a carbapenemase, such as a serine carbapenemase or a metallo-β-lactamase, or an immunogenic fragment thereof as described herein, and a pharmaceutically acceptable carrier.

Methods for administering a vaccine composition of the invention are well known in the art. It is understood that the appropriate route of administration of a vaccine can be readily determined by a skilled clinician. Exemplary routes of administration include oral administration, intramuscular injection, intradermal injection, subcutaneous injection, transdermal administration or intranasal administration. Moreover, it is understood that the formulation of the vaccine composition can be readily adjusted to accommodate the route of administration. The invention also provides that following administration of a vaccine composition of the invention, delayed, successive and/or repeated dosages of one or more antibiotic as disclosed herein may be administered to the subject.

The term "treating" or "treatment," as it is used herein is intended to mean an amelioration of a clinical symptom indicative of a bacterial infection. Amelioration of a clinical symptom includes, for example, a decrease or reduction in at least one symptom of a bacterial infection in a treated individual compared to pretreatment levels or compared to an individual with a bacterial infection. Treating also is intended to include the reduction in severity of a pathological condition, a chronic complication or an opportunistic infection which is associated with a bacterial infection. Pathological conditions, chronic complications and opportunistic infections also can be found described in, for example, Merck Manual, Sixteenth Edition, 1992, and *Acinetobacter*: Molecular Biology, Ulrike Gerischer (Editor), Caister Academic Press; 1st edition (2008).

The term "preventing" or "prevention," as it is used herein is intended to mean a forestalling of a clinical symptom indicative of a bacterial infection. Such forestalling includes, for example, the maintenance of normal physiological indicators in an individual at risk of infection by bacteria prior to the development of overt symptoms of the condition or prior to diagnosis of the condition. Therefore, preventing can include the prophylactic treatment of individuals to guard them from the occurrence of a bacterial infection. Preventing a bacterial infection in an individual also is intended to include inhibiting or arresting the development of the infection. Inhibiting or arresting the development of the condition includes, for example, inhibiting or arresting the occurrence of abnormal physiological indicators or clinical symptoms such as redness, heat, swelling and localized pain and/or others well known symptoms. Therefore, effective prevention of a bacterial infection would include maintenance of normal body temperature, weight or preventing other pathological manifestations in an individual predisposed to a bacterial infection. Individuals predisposed to a bacterial infection include an individual who is immunocompromised, for example, but not limited to, an individual with AIDS, azotemia, diabetes mellitus, diabetic ketoacidosis, neutropenia, bronchiectasis, emphysema, TB, lymphoma, leukemia, or burns, or an individual undergoing chemotherapy, bone marrow-, stem cell- and/or solid organ-transplantation or an individual with a history of susceptibility to a bacterial infection. Inhibiting or arresting the development of the condition also includes, for example, inhibiting or arresting the progression of one or more pathological conditions, chronic complications or susceptibility to an opportunistic infection associated with bacteria.

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

In some aspects of the invention, the invention methods are particularly effective for treating a bacterial infection caused by gram negative bacilli. In particular, the gram negative bacilli that are characterized as being extreme drug resistant (XDR) gram negative bacilli are susceptible to the methods of the invention. The phrase "XDR gram negative bacilli" as used herein refers to gram negative bacilli that are not susceptible to one or more of the β-lactam and quinolone antibiotics, such as cefepime, ceftazidime, imipenem, meropenem, peperacillin/tozobactam, ciprofloxacine, and levofloxacin, plus one or more of the ticarcilline-clavulanate, ampicillin-sulbactam, all aminoglycosides (including amikacin), trigecycline, and the polymyxins (colistin and polymyxin B). Accordingly, in some aspects of the invention, the XDR gram negative bacilli can be resistant to two, three, four, five, six, seven, eight, nine, ten or more different classes of antibiotics.

The criteria for determining susceptibility or resistance of bacilli to an antibiotic are well known in the art and can be readily determined by one skilled in the art. For example, the minimum inhibitory concentration (MIC) used to define susceptible stains may include the standards set forth in the European Committee on Antimicrobial Susceptibility Testing definition or Clinical and Laboratory Standards Institute definition for susceptibility breakpoints. Additional methods and criteria for determining susceptibility or resistance are described in Tato et al., *Clin. Infect. Dis.* 47:117-1178 (2007); Turnidge et al., *Clin. Microbiol. Rev.* 20:391-408 (2007); Franklin et al., *J. Clin. Microbiol.* 44:3139-3144 (2006); and Anderson et al., *J. Clin. Microbiol.* 45:2723-2725, which are herein incorporated by reference.

Several strains of gram negative bacilli are known in the art to have acquired extreme drug resistance (XDR). Non-limiting examples of such bacteria include *K. pneumoniae, S. marcescens, E. cloacae, S. enterica, K. oxytoca, Enterobacter* spp., *E. aerogenes, E. coli, P. aeruginosa, C. freundii, C. amalonaticus, C. youngae, S. flexneri, P. vulgaris, P. rettgeri,* and *M. morganii*. These exemplary bacteria have been shown to express one or more carbapenemase, such as a serine carbapenemase or a metallo-β-lactamase. Accordingly, the invention methods disclosed herein include methods for treating or preventing bacterial infections caused by gram negative bacilli that express a carbapenemase disclosed herein. Moreover, the invention methods further provide treating or preventing bacterial infections caused by *K. pneumoniae, S. marcescens, E. cloacae, S. enterica, K. oxytoca, Enterobacter* spp., *E. aerogenes, E. coli, P. aeruginosa, C. freundii, C. amalonaticus, C. youngae, S. flexneri, P. vulgaris, P. rettgeri,* or *M. morganii*.

In one embodiment, the invention provides a pharmaceutical composition having an anti-carbapenemase antibody or a fragment thereof and a pharmaceutically acceptable carrier. An anti-carbapenemase antibody includes an antibody that recognizes one or more proteins of the carbapenemase class of proteins as disclosed herein or a fragment thereof. For example, an anti-*K. pneumonia* carbapenemase (KPC) antibody of the invention has specific reactivity to a KPC protein disclosed herein, or alternatively an anti-New Delhi metallo- β-lactamase (NDM-1) antibody of the invention has specific reactivity to a NDM-1 protein disclosed herein. As disclosed in Example II, the anti-carbapenemase antibodies of the invention can also be bacterial cidal when contacted with gram negative bacteria expressing a carbapenemase, such as KPC or NDM-1.

Accordingly, an anti-serine carbapenemase antibody of the invention includes an anti-*K. pneumonia* carbapenemase (KPC) antibody, an anti-*Serratia marcescens* enzyme (SME) antibody, an anti-imipenem-hydrolyzing β-lactamase (IMI) antibody, an anti-not metalloenzyme carbapenemase (NMC-A) antibody, an anti-integron-borne cephalosporinase (IBC) antibody and an anti-Guiana extended spectrum (GES) enzyme antibody. Moreover, an anti-KPC antibody of the invention includes an anti-KPC-2 antibody, an anti-KPC-3 antibody, an anti-KPC-4 antibody, an anti-KPC-5 antibody, an anti-KPC-6 antibody, an anti-KPC-7 antibody, an anti-KPC-8 antibody, an anti-KPC-9 antibody, an anti-KPC-10 antibody and an anti-KPC-11 antibody. Still further, the invention provides that an anti-metallo-β-lactamase antibody includes an anti-New Delhi metallo-β-lactamase (NDM-1) antibody, an anti-BCII metallo-β-lactamase antibody, an anti-Verona integron-encoded (VIM) metallo-β-lactamase antibody, an anti-active on imipenem (IMP) metallo-β-lactamase antibody, an anti-German imipenemase (GIM) metallo-β-lactamase antibody and an anti-Seoul imipenemase (SIM) metallo-β-lactamase antibody. Thus, in some aspects of the invention, the pharmaceutical compositions can include one or more of the anti-carbapenemase antibody disclosed herein.

As used herein, the term "antibody" includes polyclonal and monoclonal antibodies, as well as antigen binding fragments of such antibodies. An antigen can include a native, recombinantly expressed or synthesized protein of the invention or a fragment thereof. An anti-carbapenemase antibody, or antigen binding fragment of such an antibody, is characterized by having specific binding activity for a carbapenemase protein disclosed herein or a fragment thereof of at least about $1 \times 10^5$ M$^{-1}$. Thus, Fab, Fab', F(ab')$_2$, Fabc, scFV, diabody, triabody, minibody and single-domain antibody (sdAB) fragments of an anti-carbapenemase antibody, which retain specific binding activity for a protein of the invention, are included within the definition of an antibody. Specific binding activity to a protein can be readily determined by one skilled in the art, for example, by comparing the binding activity of an anti-carbapenemase antibody to a carbapenemase disclosed herein versus a control protein that is not a protein identified herein. Methods of preparing polyclonal or monoclonal antibodies are well known to those skilled in the art (see, for example, Harlow and Lane, *Antibodies: A Laboratory Manual*, Cold Spring Harbor Laboratory Press (1988)).

In addition, an antibody useful in the present invention can be a naturally occurring antibody as well as a non-naturally occurring antibody, including, for example, a single chain antibody, a chimeric, bifunctional or humanized antibody, as well as antigen-binding fragments thereof. Such non-naturally occurring antibodies can be constructed using solid phase peptide synthesis, can be produced recombinantly or can be obtained, for example, by screening combinatorial libraries as described by Ponsel et al. (*Molecules*, 16(5):3675-3700 (2011)). These and other methods of making, for example, chimeric, humanized, CDR-grafted, single chain, and bifunctional antibodies are well known to those skilled in the art and are commercially available.

Anti-carbapenemase antibodies can be raised using an immunogenic protein as disclosed herein, which can be prepared from natural sources or produced recombinantly, or a peptide portion of the carbapenemase. Such peptide portions of the carbapenemase disclosed herein are functional antigenic fragments of the antigenic protein, which can be used to generate a carbapenemase-specific antibody. A non-immunogenic or weakly immunogenic protein or portion thereof can be made immunogenic by coupling the protein to a carrier molecule such as bovine serum albumin (BSA) or keyhole limpet hemocyanin (KLH). Various other carrier molecules and methods for coupling a protein to a carrier molecule are well known in the art (see, for example, Harlow and Lane, supra, 1988). An immunogenic protein fragment can also be generated by expressing the peptide portion as a fusion protein, for example, to glutathione S transferase (GST), polyHis or the like. Methods for expressing peptide fusions are well known to those skilled in the art (Ausubel et al., supra).

In some embodiments, the invention provides an antibody conjugate having an antibody or fragment thereof conjugated to a siderophore or an analog thereof. In this embodiment, the antibody or fragment thereof comprising the antibody conjugate may be raised against any desired antigen including, but not limited to, a carbapenemase disclosed herein. Such an antibody or fragment thereof can be generated using methods well known in art including those disclosed here. As disclosed above, an antigen can include any native, recombinantly expressed or synthesized protein or a fragment thereof that is desired to be the target for the antibody conjugate. Similarly, the antibody conjugates of the invention also includes antibody fragments conjugated to a siderophore or an analog thereof, wherein the antibody fragment is selected from a Fab, a Fab', a F(ab')$_2$, a Fabc, a scFV, a diabody, a triabody, a minibody and a single-domain antibody (sdAB) fragment.

The antibody conjugates of the invention also include a siderophore or an analog thereof conjugated to the antibody. A "siderophore" as used herein refers to a low molecular weight compound produced by a microorganism that binds ferric iron extracellularly to form a stable chelate for transport back into the microorganism. Siderophores are typically produced by a microorganism during growth in iron depleted conditions in order to isolate the required amount of iron needed for survival. Moreover, excess iron can increase the virulence of a variety of microorganisms including species from the following genera: *Escherichia, Klebsiella, Listeria, Neisseria, Pasteurella, Shigella, Salmonella, Vibrio* and *Yersinia*. Siderophores have been isolated from a diverse array of microorganisms including, but not limited to, *Salmonella typhimurium, Escherichia coli, Pseudomonas aeruginosa, Klebsiella pneumoniae, Klebsiella oxytoca, Neisseria meningitides, Neisseria gonorrhoeae, Enterobacter cloacae, Salmonella enterica, Enterobacter aerogenes, Citrobacter* spp. and *Shigella flexneri*. Accordingly, in some aspects of the invention, an antibody conjugate disclosed herein can be conjugated with any of the siderophores known in the art. For example, siderophores that can be conjugated with an antibody of the invention include an enterobactin, a bacillibactin, a vibrobactin, a ferrichrome, a desferrioxamine, a fusarinine C, an ornibactin, an azotobactin, a pyoverdine and a yersiniabactin. In some aspects, the invention also provides that the siderophore or analog thereof conjugated to the antibody of the invention can be the siderophore produced by the target microorganism causing or likely to cause a bacterial infection of a given subject. For example, if a subject is known to have or is susceptible to an infection caused by XDR *Klebsiella pneumoniae*, the antibody conjugate of the invention that can be administered to the subject includes a siderophore or analog thereof that is naturally produced by *Klebsiella pneumoniae* under iron depleted conductions.

The invention also provides, in some aspects, an antibody or fragment thereof conjugated with a siderophore analog. The term "analog" as used herein refers to a chemical compound that has a similar structure and similar chemical properties to those of another compound, but differs from it by one or more element or group. Accordingly, when used in reference to a siderophore, a siderophore analog can differ from the naturally produced siderophore by one or more element or group, but maintains the chemical property of binding ferric iron and/or transporting into a microorganism. The compounds 1,2-hopobactin, pyridinochelin, and N,N',N"-tris(2,3-dihydroxybenzoyl)-1,1,1-tris(aminomethyl)ethane, for example, are all analogs of enterobactin. Additionally, exemplary enterobactin analogs are described in U.S. Pat. Nos. 4,631,291 and 5,412,080, which are herein incorporated by reference.

Conjugating a siderophore to an antibody of the invention can be done using several methods that are well known in the art. For example, as disclosed in Examples III and IV, a siderophore disclosed herein, such as enterobactin, can be conjugated to an antibody or an Fabc fragment using a thiosulfate cross-linker, wherein the enterobactin is covalently bonded to the antibody or Fabc fragment through a bivalent thiosulfate bond at cysteine residues in the antibody. Additional methods for generating an antibody/siderophore conjugate of the invention can be adopted from methods used to generate siderophore-antibiotic conjugates as exemplified in Budzikiewicz, Curr. Top. Med. Chem. 1(1):73-82 (2001).

Accordingly, in some embodiments, the invention provides a pharmaceutical composition having an anti-carbapenemase antibody conjugated to a siderophore or an analog thereof. The antibody conjugate included in the pharmaceutical composition of the invention can comprise any one of the anti-carbapenemase antibodies disclosed herein, such as an anti-serine carbapenemase antibody or an anti-metallo-$\beta$-lactamase antibody, conjugated to any one of the siderophores disclosed herein. Thus, in some aspects of the invention, a siderophore conjugated to the anti-carbapenemase antibody is selected from an enterobactin, a bacillibactin, a vibrobactin, a ferrichrome, a desferrioxamine, a fusarinine C, an ornibactin, an azotobactin, a pyoverdine and a yersiniabactin. In some aspects, the siderophore can be conjugated to the anti-carbapenemase antibody through a bivalent thiosulfate linker.

In another embodiment, the invention provides a method for treating or preventing a bacterial infection in a subject in need thereof by administering a therapeutically effective amount of a pharmaceutical composition disclosed herein to the subject. For example, the pharmaceutical composition can include one or more anti-carbapenemase antibodies disclosed herein or a fragment thereof. Accordingly, in some aspects, the invention provides a method for treating or preventing a bacterial infection in a subject in need thereof by administering a therapeutically effective amount of a pharmaceutical composition having an anti-carbapenemase antibody, such as an anti-serine carbapenemase antibody or an anti-metallo-$\beta$-lactamase antibody, or a fragment thereof as described herein, and a pharmaceutically acceptable carrier.

Methods for administering a pharmaceutical composition of the invention are well known in the art. It is understood that the appropriate route of administration of a pharmaceutical composition can be readily determined by a skilled clinician. Exemplary routes of administration include oral administration, intramuscular injection, intradermal injection, subcutaneous injection, transdermal administration or intranasal administration. Moreover, it is understood that the formulation of the pharmaceutical composition can be readily adjusted to accommodate the route of administration. The invention also provides that following administration of a pharmaceutical composition of the invention, delayed, successive and/or repeated dosages of one or more antibiotic as disclosed herein may be administered to the subject.

In one aspect of the invention methods, the methods further include administering a therapeutically effective amount of an antibiotic. In this aspect, the administration of a vaccine composition or pharmaceutical composition disclosed herein can increase the susceptibility of the gram negative bacteria to the co-administered antibiotic by creating a synergistic effect between the anti-carbapenemase antibody and the antibiotic. The vaccine and pharmaceutical compositions of the invention are particularly effective in increasing or restoring the bacterial cidal activity of $\beta$-lactam antibiotics. Accordingly, the methods of the invention can include administering a therapeutically effective amount of a $\beta$-lactam antibiotic, such as, but not limited to, a penicillin, a cephalosporin, a cephamycine, a carbapenem, a penem, a monobactam and a $\beta$-lactamase inhibitor. In some aspects, the carbapenem administered in the invention methods is selected from imipenem, meropemem, ertapemem, doripenem, panipenem, biapemem and tebipenem. In another aspect of the invention, the penem administered in the invention methods is farapenem.

The "therapeutically effective amount" will vary depending on the vaccine and pharmaceutical composition used, the co-administered antibiotic used, the disease and its severity and the age, weight, etc., of the subject to be treated, all of which is within the skill of the attending clinician. It is contemplated that a therapeutically effective amount of one or more of the vaccine or pharmaceutical compositions described herein will alter the pathogenicity of gram negative bacteria. Similarly, a therapeutically effective amount of an antibiotic co-administered with a composition disclosed herein will alter the pathogenicity of the gram negative bacteria. A therapeutically effective amount is distinguishable from an amount having a biological effect. A vaccine or pharmaceutical composition of the present invention may have one or more biological effects in vitro or even in vivo, such as reducing the function of a protein or polypeptide expressed by a gram negative bacteria. A biological effect, however, may not result in any clinically measurable therapeutically effect as described herein as determined by methods within the skill of the attending clinician.

In another embodiment, the invention methods for treating or preventing a bacterial infection in a subject in need thereof includes administering an agent that decreases or lowers the free iron available to infecting bacilli. For example, the pharmaceutical composition can include one or more agent that binds to and/or chelates free iron. Non-limiting agents that can be used to decrease or lower iron levels in a subject include dimercaptosuccinic acid (DMSA), 2,3-dimercapto-1-propanesulfonic acid (DMPS), inositol hexaphosphate (IP6) and alpha lipoic acid (ALA). Without being bound by theory, it is contemplated that the administration of such agents will reduce the available iron for the infecting bacilli, which will thereby increase the expression of the siderophore receptors of the bacilli. The increased siderophore receptors will subsequently increase the available receptors for binding siderophores conjugated to the antibody conjugates of the invention. Accordingly, in some aspects, the invention provides a method for treating or preventing a bacterial infection in a subject in need thereof by administering a therapeutically effective amount of a pharmaceutical composition as disclosed herein and one or more agent that binds to and/r chelates free iron. The invention also provides administering one or more of these agents prior to administration of a pharmaceutical composition of the invention.

In one embodiment, the invention provides a method for increasing or restoring the efficacy of an antibiotic. In this aspect, the method can include contacting a bacterial cell with an effective amount of an anti-carbapenemase antibody as disclosed herein, such as an anti-serine carbapenemase antibody or an anti-metallo-β-lactamase antibody. The invention also provides that the antibiotic used in the invention method can be a β-lactam antibiotic. The invention further provides that the bacterial cell may express a carbapenemase as disclosed herein, such as, but not limited to, a serine carbapenemase or a metallo-β-lactamase. It is understood that the invention method for increasing or restoring the efficacy of an antibiotic can be performed either in vitro or in vivo.

An "effective amount" is an amount sufficient to effect beneficial or desired results. Contacting with an effective amount can include one or more administrations, applications or dosages. For example, following administration of a vaccine composition or pharmaceutical composition of the invention, delayed, successive and/or repeated dosages of one or more antibiotic may be administered to the subject. Moreover, it is understood that delivery is dependent on a number of variables including the time period for which the individual dosage unit is to be used, the bioavailability of the antibody and/or antibiotic, the route of administration, etc. It is understood, however, that specific dose levels of the antibody and/or antibiotic of the present invention for any particular subject or purpose depends upon a variety of factors including the activity of the specific antibody and/or antibiotic employed, the time of administration, the rate of excretion, the drug combination, and the form of administration. In general, one will desire to administer an amount of the antibody or antibody fragment compositions of this invention to increase the bacterial cidal activity of a co-administered antibiotic either in vitro or in vivo by at least 10%, 25%, 40%, 60%, 80%, 90% or 95% as compared to control. Determination of these parameters is well within the skill of the art. These considerations, as well as effective formulations and administration procedures are well known in the art.

In some aspects of the invention methods, the β-lactam antibiotic that is targeted for increased or restored efficacy is selected from a penicillin, a cephalosporin, a cephamycine, a carbapenem, a penem, a monobactam and a β-lactamase inhibitor. In some aspects, the carbapenem contacted to the bacterial cell in the invention methods is selected from the group consisting of imipenem, meropemem, ertapemem, doripenem, panipenem, biapemem and tebipenem. In another aspect of the invention, the penem used in the methods is farapenem.

In some aspects of the invention methods, the anti-carbapenemase antibody used to increase the efficacy of the antibiotic is an antibody conjugate as disclosed herein, such as an anti-serine carbapenemase antibody or an anti-metallo-β-lactamase antibody conjugated to a siderophore or an analog thereof.

It is understood that modifications which do not substantially affect the activity of the various embodiments of this invention are also provided within the definition of the invention provided herein. Accordingly, the following examples are intended to illustrate but not limit the present invention.

Example I rKPC and rNDM-1 Immunization

A vaccination program targeting KPC- and NDM-1 was developed. The KPC gene was cloned from a pan-resistant (to all antibiotics, including colistin) clinical lung isolate of *K. pneumoniae* acquired at a local hospital (KPC-KP1) and the NDM-1 gene was cloned from a clinical *K. pneumoniae* isolate (ATCC BAA-2146). Recombinant KPC (rKPC) and recombinant NDM-1 (rNDM-1) proteins were expressed, purified, and used for immunization of mice. The immunization of the mice consisted of subcutaneously injecting either rKPC or rNDM-1 with $Al(OH)_3$ adjuvant. A booster immunization for each mouse was administered at three weeks post initial immunization. Two weeks after the booster, serum from immune and control mice were harvested. Mice immunized with rKPC or NDM-1 showed a marked increase in anti-KPC and anti-NDM-1 IgG titers as compared to control mice (FIG. 1). Thus, high titers of immune polyclonal antibodies have been generated against KPC and NDM-1.

Example II

Antibacterial Activity of Anti-rKPC and rNDM-1 Antibodies

Figure 2:
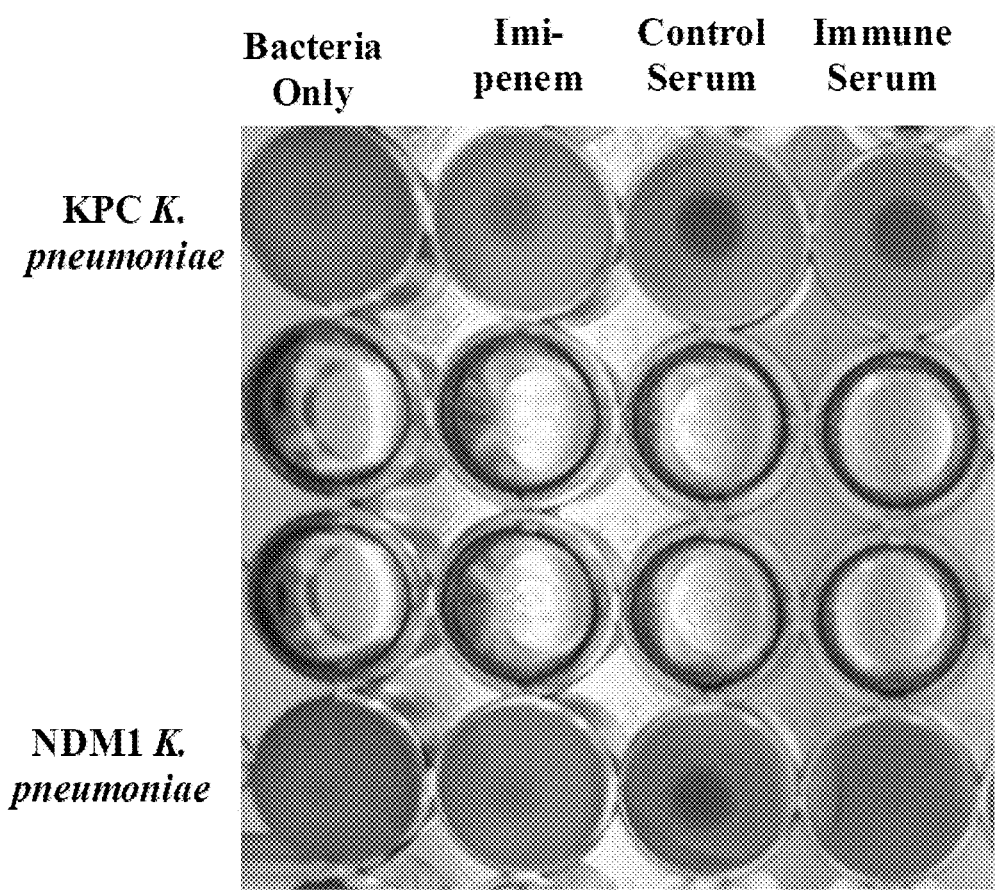
FIG. 2 shows that anti-NDM-1 immune serum killed NDM-1-expressing *K. pneumoniae* in vitro, but anti-KPC immune serum did not kill KPC-expressing *K. pneumoniae*. Standard CLSI media, bacterial inocula, and culture conditions were used.

To determine the in vitro effects of the antibody generated in response to rNDM1 and rKPC vaccination, bacteria were incubated overnight at 37° C. in 10% serum plus Mueller-Hinton broth, per CLSI standards. A KPC-expressing *Klebsiella pneumoniae* strain KPC-KP1 (clinical lung isolate, resistant to all antibiotics, including colistin, with an imipenem MIC>32 µg/ml), and NDM-1-expressing *K. pneumoniae* (ATCC BAA-2146) (clinical isolate resistant to all antibiotics except colistin and tigecycline, with an imipenem MIC>32 µg/ml) were used to assess the antibacterial activity of the serum obtained from immunized mice. Immune but not control serum killed NDM-1-*K. pneumoniae* but did not kill KPC-*K. pneumoniae* (FIG. 2). Thus, the immune serum was directly cidal for NDM-1 expressing *K. pneumoniae*.

Example III

Generation of Iron Siderophore Conjugated Antibody Fragments

Based on the antibacterial activity of the serum obtained from the immunized mice, it was contemplated that the primary limitation of the antibody to neutralize carbapenemase activity was the inability of the antibody to penetrate through the outer gram negative bacilli membrane to reach the periplasmic space. To enhance bacterial cell uptake, IgG was purified from immune and control sera using a standard protein A column, per the manufacturer's instructions (Pierce). Purified anti-KPC and anti-NDM-1 immune IgG, as well as control IgG, were covalently conjugated to the gram negative bacilli iron siderophore enterobactin (Sigma) using a commercially available thiosulfate cross-linker (ThermoScientific) per the manufacturer's instructions. Formal minimum inhibitory concentration (MIC) testing was conducted using the antibody conjugated to enterobactin.

Bacteria were cultured in Mueller-Hinton broth overnight using standard CLSI procedures. Immune IgG linked to enterobactin was diluted 2-fold across the plates and growth inhibition was visually determined in the wells. Immune IgG conjugated to enterobactin had an MIC of 2.5 µg/ml against NDM-1-expressing *K. pneumoniae*, whereas control IgG conjugated to enterobactin had no detectable MIC at concentrations as high as 128 µg/ml. However, KPC-expressing strains were not killed by immune IgG-enterobactin conjugates.

Example IV

Antibacterial Activity of Iron Siderophore Conjugated Antibody Fragments

Figure 3:
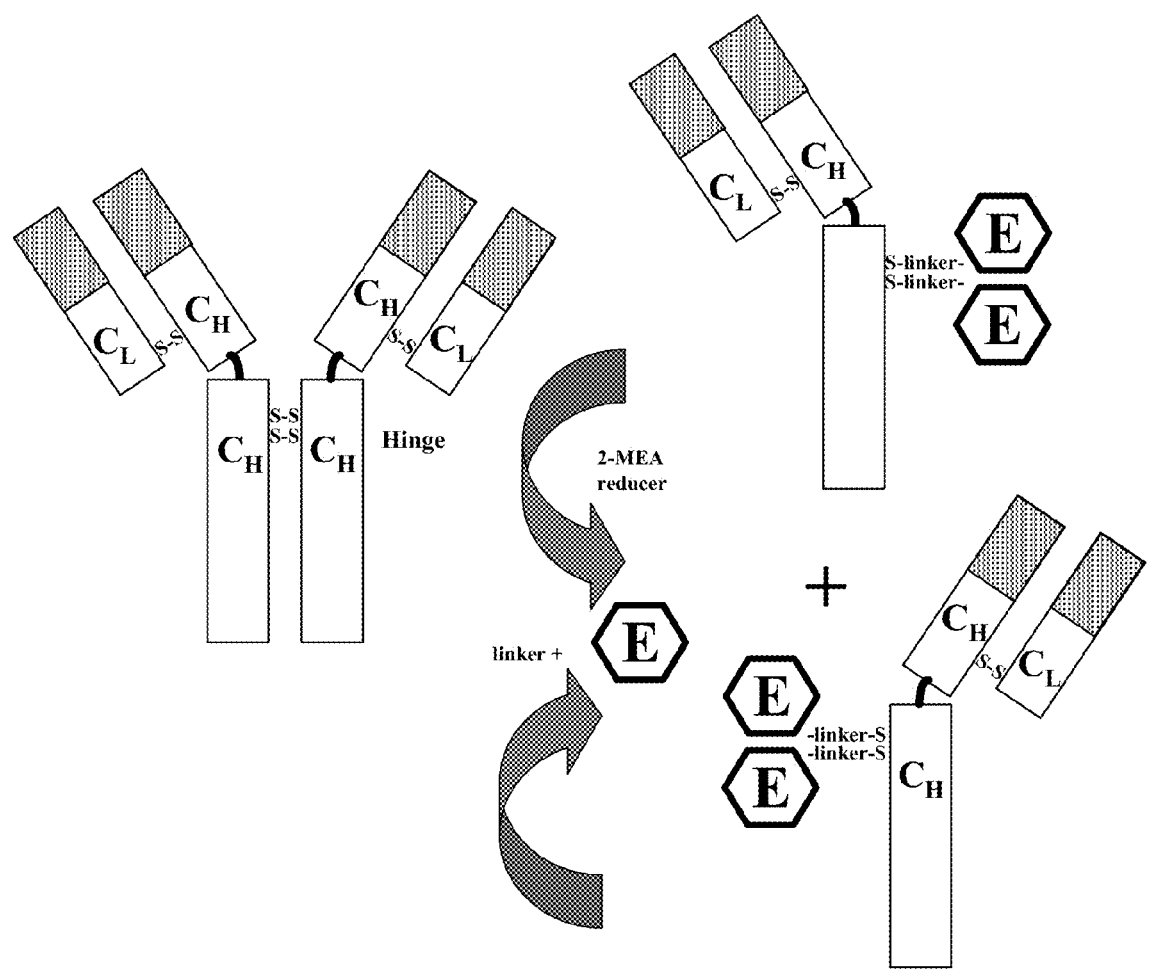
FIG. 3 shows a schematic representation of the method used to generate Fabc fragments from IgG. 2-mercaptoethylamine (2-MEA) was used to preferentially reduce IgG hinge disulfide bonds rather than heavy-light chain disulfide bonds. After reduction, a bivalent thiosulfate linker and enterobactin (E) were sequentially added to create Fabc-enterobactin conjugates.

To further enhance uptake of the IgG-siderophore conjugate, the hinge region disulfide bonds of the IgG heavy chain were reduced using 2-mercaptoethylamine (2-MEA), which when used at concentrations recommended by the manufacturer preferentially reduces the hinge region disulfide bonds, rather than the light chain-heavy chain disulfide bonds (FIG. 3). Stimmel et al., *J. Biol. Chem.* 275:30445-30450 (2000). The reduction thus generated two IgG Fabc fragments per IgG molecule. Studies using non-denatured gels after reduction confirmed that while small amounts of free light chain (25 kD) and free heavy chain (50 kD) were generated by the reduction, the majority of the protein (>80%) was Fabc fragments (75 kD). A small amount of whole IgG (150 kD) was also seen. After the reduction step, the Fabc fragments were covalently conjugated with enterobactin as above.

Figure 4:
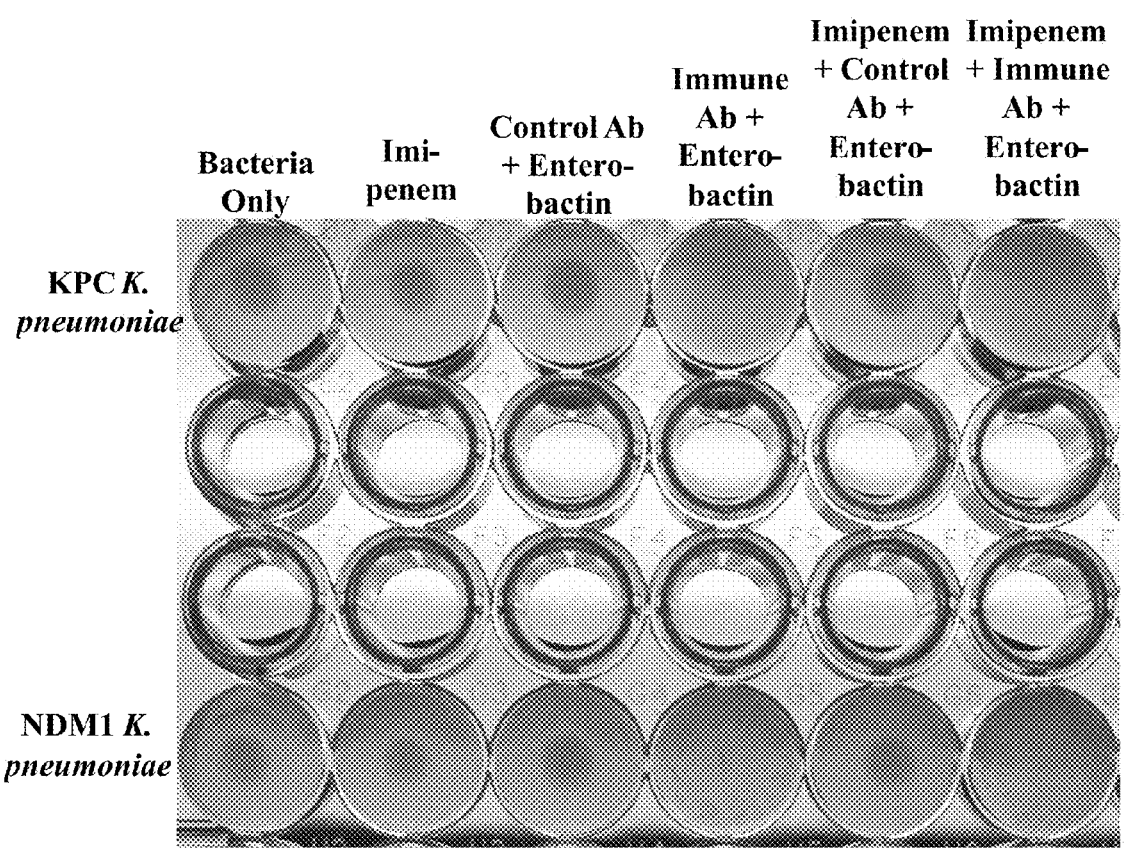
FIG. 4 shows that enterobactin conjugation of immune Fabc dimers killed KPC- and NDM-1-expressing *K. pneumoniae*. IgG purified from immune and control serum was reduced at the hinge region to separate IgG tetramers into Fabc dimers. Enterobactin was covalently linked to the dimers. Bacteria were killed after overnight culture with the enterobactin-linked immune but not control dimers.

Growth was inhibited for both KPC- and NDM-1 expressing *K. pneumoniae* cultured overnight with 2 µg/ml of Fabc-enterobactin (FIG. 4). Synergy with imipenem (8 µg/ml) was difficult to detect because the Fabc-siderophore complexes inhibited bacterial growth even without the imipenem. However, a small amount of residual bacterial growth was seen in the wells without synergy imipenem, whereas no growth was seen in wells containing imipenem (compare wells in the 4$^{th}$ vs. 6$^{th}$ column in FIG. 4). Accordingly, synergistic killing of bacteria was occurring when imipenem was added to the IgG-siderophore conjugate.

Finally, when the reduction step was repeated using a 10-fold higher relative concentration of 2-MEA to IgG, non-denatured gels confirmed that all chains were dissociated, and the predominant proteins seen were 25 kD light chains and 50 kD heavy chains, with minimal 75 kD Fabc fragments seen. The fully reduced light chain and heavy chain product was cross-linked to enterobactin and had no detectable MIC against either KPC- or NDM-1-expressing bacteria.

These results indicate that intact Fabc fragments can be bacterial cidal when conjugated to enterobactin, and that light chains or heavy chains alone cannot inhibit bacterial growth. Thus, when immune IgG was covalently linked to an iron siderophore, and particularly when smaller IgG Fabc fragments were used, the conjugated complexes inhibited bacterial growth in vitro.

Example V

In Vivo Therapeutic Activity of Anti-KPC and Anti-NDM-1 Antibodies

Figure 5:
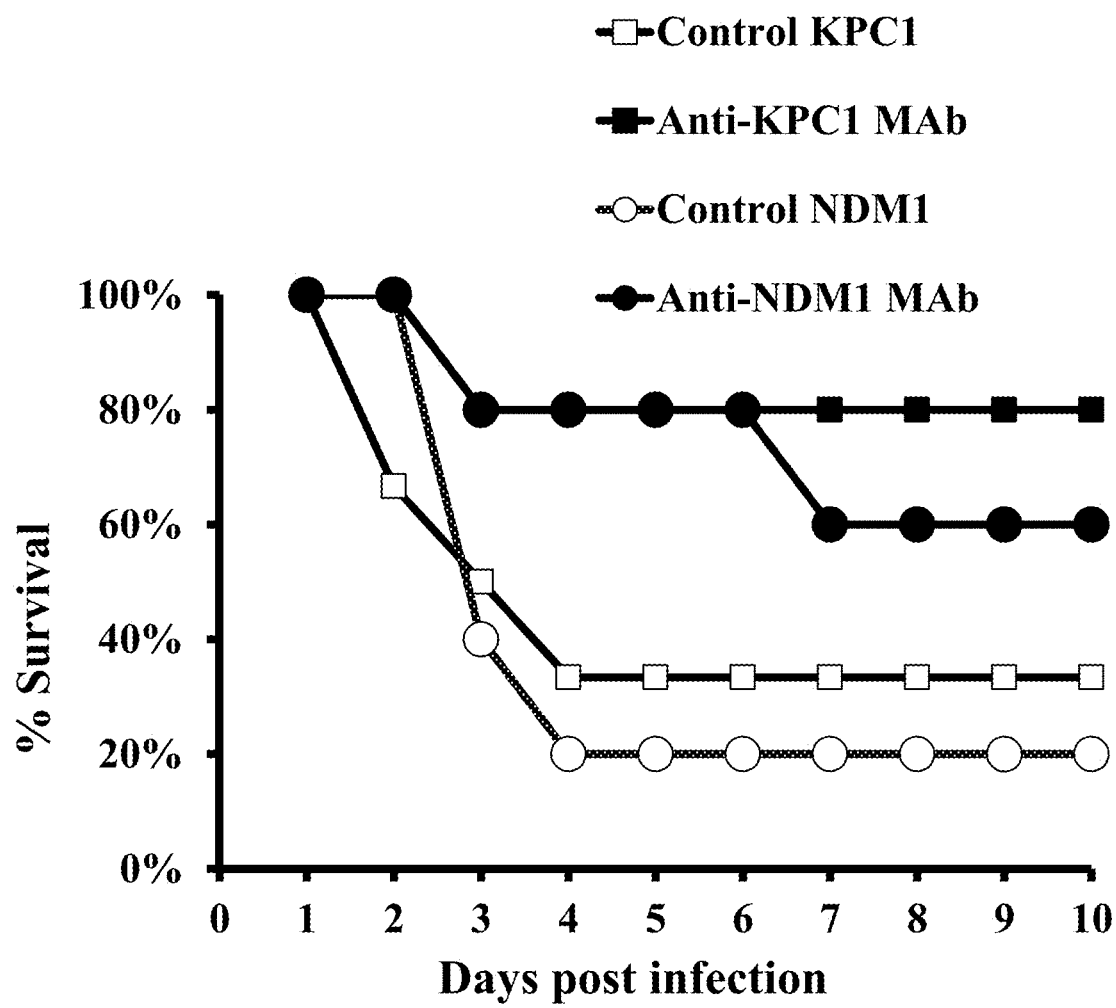
FIG. 5 shows a survival plot for mice infected with KPC-1 (also known as KPC-2) or NDM-1 following administration of anti-KPC-1 or anti-NDM-1 monoclonal antibodies (Mab).

To demonstrate the in vivo therapeutic activity of anti-serine carbapenemase and anti-metallo-β-lactamase monoclonal antibodies (MAbs), mice were infected via the tail-vein with KPC-1 (also known as KPC-2) or NDM-1 expressing bacteria. The infected mice were then treated one hour later by intraperitoneal injection with a single 200 µg dose of either anti-KPC-1 or anti-NDM-1 MAbs depending upon which type of bacteria was used to infect the mice, i.e. anti-KPC-1 MAbs were used to treat KPC-1 infected mice and anti-NDM-1 MAbs were used to treat NDM-1 infected mice. Mice treated with either anti-KPC-1 or anti-NDM-1 MAbs had significantly improved survival compared to control mice treated with isotype control antibody (FIG. 5). These results demonstrate that anti-serine carbapenemase and anti-metallo-β-lactomase MAbs can be used to treat bacterial infections.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A pharmaceutical composition comprising an anti-serine carbapenemase antibody or a binding fragment thereof and a pharmaceutically acceptable carrier, wherein said anti-serine carbapenemase antibody is an anti-*K. pneumonia* carbapenemase (KPC) antibody selected from the group consisting of an anti-KPC-3 antibody, anti-KPC-4 antibody, anti-KPC-5 antibody, anti-KPC-6 antibody, anti-KPC-7 antibody, anti-KPC-8 antibody, anti-KPC-9 antibody, anti-KPC-10 antibody and an anti-KPC-11 antibody.

2. A pharmaceutical composition comprising an anti-serine carbapenemase antibody or a binding fragment thereof and a pharmaceutically acceptable carrier, wherein said anti-serine carbapenemase antibody is conjugated to a siderophore or an analog thereof.

3. The pharmaceutical composition of claim 2, wherein said siderophore is selected from the group consisting of enterobactin, bacillibactin, vibrobactin, ferrichrome, desferrioxamine, fusarinine C, omibactin, azotobactin, pyoverdine and yersiniabactin.

4. An antibody conjugate comprising an anti-serine carbapenemase antibody or binding fragment thereof conjugated to a siderophore or an analog thereof, wherein said siderophore is selected from the group consisting of enterobactin, bacillibactin, vibrobactin, ferrichrome, fusarinine C, omibactin, azotobactin, pyoverdine and yersiniabactin.

5. A pharmaceutical composition comprising an anti-serine carbapenemase antibody or a binding fragment thereof and a pharmaceutically acceptable carrier, wherein said anti-serine carbapenemase antibody is selected from the group consisting of an anti-*Serratia marcescens* enzyme (SME) antibody, an anti-imipenem-hydrolyzing β-lactamase (IMI) antibody, an anti-integron-borne cephalosporinase (IBC) antibody and an anti-Guiana extended spectrum (GES) enzyme antibody.

6. The pharmaceutical composition of claim 5, wherein said anti-serine carbapenemase antibody is conjugated to a siderophore or an analog thereof.

7. The pharmaceutical composition of claim 6, wherein said siderophore is selected from the group consisting of enterobactin, bacillibactin, vibrobactin, ferrichrome, desferrioxamine, fusarinine C, omibactin, azotobactin, pyoverdine and yersiniabactin.

8. The pharmaceutical composition of claim 7, wherein said siderophore is enterobactin.

9. The pharmaceutical composition of claim 6, wherein said siderophore is conjugated to said antibody at a bivalent thiosulfate linker.

10. The pharmaceutical composition of claim 5, wherein said antibody binding fragment is selected from the group consisting of a Fab, a Fab', a F(ab')2, a Fabc, a scFV, a diabody, a triabody, minibody and a single-domain antibody (sdAB).

11. The pharmaceutical composition of claim 10, wherein said antibody binding fragment is a Fabc.

12. The pharmaceutical composition of claim 3, wherein said siderophore is enterobactin.

13. The pharmaceutical composition of claim 3, wherein said siderophore is conjugated to said antibody at a bivalent thiosulfate linker.

14. The pharmaceutical composition of claim 2, wherein said antibody binding fragment is selected from the group consisting of a Fab, a Fab', a F(ab')2, a Fabc, a scFV, a diabody, a triabody, minibody and a single-domain antibody (sdAB).

15. The pharmaceutical composition of claim 14, wherein said antibody binding fragment is a Fabc.

16. The antibody conjugate of claim 4, wherein said siderophore is enterobactin.

17. The antibody conjugate of claim 4, wherein said siderophore is conjugated to said antibody at a bivalent thiosulfate linker.

18. The antibody conjugate of claim 4, wherein said antibody binding fragment is selected from the group consisting of a Fab, a Fab', a F(ab')2, a Fabc, a scFV, a diabody, a triabody, minibody and a single-domain antibody (sdAB).

19. The antibody conjugate of claim 18, wherein said antibody binding fragment is a Fabc.

20. The antibody conjugate of claim 4, wherein said anti-serine carbapenemase antibody is selected from the group consisting of an anti-*K. pneumonia* carbapenemase (KPC) antibody, an anti-*Serratia marcescens* enzyme (SME) antibody, an anti-imipenem-hydrolyzing β-lactamase (IMI) antibody, an anti-integron-borne cephalosporinase (IBC) antibody and an anti-Guiana extended spectrum (GES) enzyme antibody.

21. The antibody conjugate of claim 4, wherein said anti-serine carbapenemase antibody is selected from the group consisting of an anti-*Serratia marcescens* enzyme (SME) antibody, an anti-imipenem-hydrolyzing 13-lactamase (IMI) antibody, an anti-integron-borne cephalosporinase (IBC) antibody and an anti-Guiana extended spectrum (GES) enzyme antibody.

22. The antibody conjugate of claim 4, wherein said anti-serine carbapenemase antibody is an anti-KPC antibody.

23. The pharmaceutical composition of claim 22, wherein said anti-KPC antibody is selected from the group consisting of an anti-KPC-2 antibody, anti-KPC-3 antibody, anti-KPC-4 antibody, an anti-KPC-5 antibody, an anti-KPC-6 antibody, an anti-KPC-7 antibody, an anti-KPC-8 antibody, an anti-KPC-9 antibody, an anti-KPC-10 antibody and an anti-KPC-11 antibody.

24. The pharmaceutical composition of claim 1, wherein said antibody binding fragment is selected from the group consisting of a Fab, a Fab', a F(ab')2, a Fabc, a scFV, a diabody, a triabody, minibody and a single-domain antibody (sdAB).

25. The pharmaceutical composition of claim 24, wherein said antibody binding fragment is a Fabc.

26. The pharmaceutical composition of claim 1, wherein the antibody is a monoclonal antibody.

27. The pharmaceutical composition of claim 26, wherein the antibody is a humanized monoclonal antibody.

28. A method for treating a bacterial infection in a subject in need thereof comprising administering a therapeutically effective amount of a pharmaceutical composition of claim 1 or 5 to said subject.

29. A method for increasing the efficacy of an antibiotic comprising contacting a bacterial cell with an effective amount of the pharmaceutical composition of claim 1 or 5, wherein said antibiotic is β-lactam antibiotic and said bacterial cell expresses a serine carbapenemase.

* * * * *